United States Patent
Pinhas et al.

[11] 3,963,758
[45] June 15, 1976

[54] 2-(BENZOFUROYL)PHENYL ACETIC ACIDS

[75] Inventors: Henri Pinhas, Paris; Monique Susini, Bretigny, both of France

[73] Assignee: Serdex - Societe d'Etudes, de Recherches, de Diffusion et d'Exploitation, Puteaux, France

[22] Filed: June 14, 1974

[21] Appl. No.: 480,135

[30] Foreign Application Priority Data
June 26, 1973 United Kingdom............ 30196/73

[52] U.S. Cl............... 260/346.2 R; 424/285
[51] Int. Cl.²............................ C07D 307/78
[58] Field of Search................. 260/346.2 R

[56] References Cited
UNITED STATES PATENTS
3,578,683  5/1971  Loy et al................. 260/346.2 R OTHER PUBLICATIONS
Mustafa– The Chemistry of Heterocyclic Compounds– vol. 29 Benzofurans–John Wiley and Sons; 1974, pp. 85 and 115.

Primary Examiner—Henry R. Jiles
Assistant Examiner—Bernard Dentz
Attorney, Agent, or Firm—Young & Thompson

[57] ABSTRACT

The compounds of formula

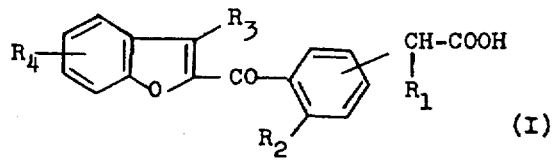

(I)

in which $R_1$ represents a hydrogen atom or an alkyl radical having 1–6 carbon atoms, $R_2$ represents a hydrogen atom or an alkyl radical having 1–6 carbon atoms, an alkoxy radical having 1–6 carbon atoms or a halogen atom, $R_3$ represents a hydrogen atom or an alkyl radical having 1–6 carbon atoms or an aryl radical, and $R_4$ represents a hydrogen atom or an alkyl radical having 1–6 carbon atoms, an alkoxy radical having 1–6 carbon atoms, a hydroxy radical, a halogen atom or a trifluoromethyl radical, and their pharmacologically acceptable salts and esters possess analgesic and anti-inflammatory properties.

4 Claims, No Drawings

2-(BENZOFUROYL)PHENYL ACETIC ACIDS

This invention relates to new phenyl acetic acid derivatives, to a process for their preparation and to the applications thereof, particularly in human medicine.

Said compounds possess particularly advantageous therapeutically useful analgesic and anti-inflammatory properties.

The new derivatives of this invention have the following general formula:

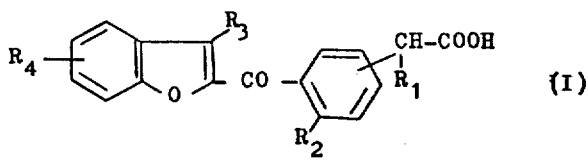

in which:

$R_1$ represents a hydrogen atom or an alkyl radical having 1–6 carbon atoms, typically a methyl radical, $R_2$ represents a hydrogen atom or an alkyl radical having 1–6 carbon atoms, an alkoxy radical having 1–6 carbon atoms or a halogen atom, typically a chlorine, fluorine or bromine atom, $R_3$ represents a hydrogen atom or an alkyl radical having 1–6 carbon atoms or an aryl radical, typically an optionally substituted phenyl radical, $R_4$ represents a hydrogen atom or an alkyl radical having 1–6 carbon atoms, an alkoxy radical having 1–6 carbon atoms, a hydroxy radical, a halogen atom, typically a chlorine, fluorine or bromine atom, or a trifluoromethyl radical.

This invention relates also to the pharmacologically acceptable esters (typically with lower alkanols) and salts of acids of the formula (I) (such as the sodium, potassium, magnesium and like salts).

This invention includes also within its scope a process for the preparation of compounds of the formula (I), comprising reacting an ortho-hydroxy-carbonyl derivative of the general formula (II):

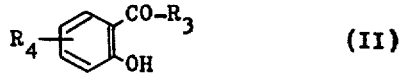

in which $R_3$ and $R_4$ have the above-defined meanings, with a (α-halogeno-acetyl)aryl acetic derivative of the general formula:

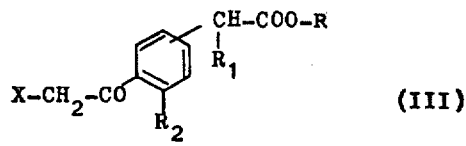

in which $R_1$ and $R_2$ have the above-defined meanings, R is a lower alkyl radical and X is halogen, to give [(2-benzofuroyl)aryl]-acetic esters which may be purified by distillation and which, on saponification, give the corresponding acids.

Compounds (II) are generally commercially available materials or may be prepared by conventional techniques described in the chemical literature.

The derivatives having the formula (III) may be obtained by halogenation of the corresponding acetyl derivatives, having the formula

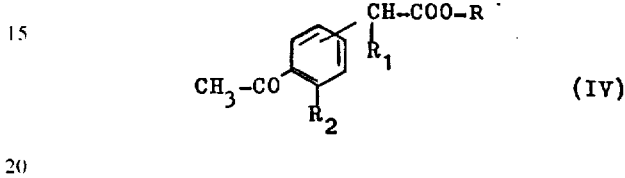

in which R, $R_1$ and $R_2$ have the aforesaid meanings.

This reaction is particularly easy in the case of the bromo derivatives which may be obtained by a conventional technique by action of bromine.

The derivatives having the formula (IV) may in turn be prepared by a Friedel-Crafts reaction between the corresponding aryl acetic derivatives and acetyl chloride. This reaction is conducted in the presence of aluminum chloride. The solvents generally used are carbon disulfide, methylene chloride, 1,2-dichloro-ethane, and the like.

When $R_2$ is hydrogen and $R_1$ is hydrogen, there is obtained a mixture of para- and meta-acetyl aryl acetic derivatives which are readily separated according to a method described in the literature (J.A.C.S., 1946, 68, 2133).

When $R_2$ is hydrogen and $R_1$ is an alkyl radical, the separation of the para- and meta-acetyl aryl acetic derivatives is effected according to conventional techniques. A spinning band distillation column may be used, for example. The ester mixture may also be converted to an acid mixture, by alkaline or acidic saponification and, by fractional crystallization of this mixture, it is also possible to obtain the pure para- and meta-acid isomers which are then esterified to the corresponding ethyl esters, for example.

The condensation of compounds (II) and (III) is advantageously effected by refluxing an equimolar mixture of compounds of the formula (II) and (III) in an organic solvent, generally alcohol or acetone, in the presence of an alkaline agent such as sodium or potassium carbonate or sodium or potassium bicarbonate.

When, in the general formula (I), $R_1$ is alkyl, there is an asymmetrical carbon atom in α position to the carboxylic group. The two optical isomers may be isolated according to a technique known in the literature, comprising converting this racemic acid to a salt with a l- or d- optically active amine (such as α-methyl benzylamine, for example).

The following non limiting examples illustrate the preparation of compounds according to this invention.

EXAMPLE 1

2-[3-(2-benzofuroyl)-phenyl]-propionic acid

I. $R_1 = CH_3$; $R_2 = R_3 = R_4 = H$ a. Preparation of the mixture of ethyl 2-(para- and meta-acetyl phenyl)-propionate To a thoroughly stirred suspension of aluminum chloride (1.2 mole) in methylene chloride (0.5 liter) cooled to about −10°C, are slowly added ethyl 2-phenyl propionate (0.3 mole) in methylene chloride solution followed by acetyl chloride (1.2 mole) in methylene chloride solution. The temperature of the reaction medium should not exceed 10°C during the addition of the reagents. On completion of the addition, stirring is continued for a further 24 hours at room temperature.

The reaction medium is then poured over an ice-hydrochloric acid mixture (about 50 cc). The aqueous phase is decanted and re-extracted with methylene chloride, after which the combined organic phases are washed with water until a neutral pH is obtained.

The material is dried over sodium sulfate and the solvent is removed. The resulting oily residue is distilled.

The para-meta mixture distills under a pressure of 1 mm Hg between 140° and 145°C (Yield: 52%).

b. Separation of the mixture of ethyl 2-(para- and meta-acetyl phenyl)propionate Fractional distillation is effected by means of a spinning band distillation column. The meta isomer distills first. The purity of each fraction is controlled by gas chromatography.

Both the para- and meta-derivatives are clear oils.

c. Preparation of ethyl 2-[meta-(α-bromo-acetyl)-phenyl]propionate

To a cooled vigorously stirred mixture containing ethyl 2-(m-acetyl phenyl)propionate (0.1 mole) dissolved in dry ether (100 ml) and a pinchful of aluminum chloride is added dropwise 0.1 mole bromine.

On completion of the addition, the reaction mixture is stirred for a further hour at room temperature. The mixture is poured over an ice+water mixture and is then extracted with ether, washed with water to neutral pH, dried and the ether is evaporated off, to give a clear yellow oil which is used as the crude material.

d. Preparation of ethyl 2-[3-(2-benzofuroyl)-phenyl]-propionate

Ethyl 2-[meta-(α-bromo-acetyl)-phenyl]propionate (0.1 mole) is mixed with dry potassium carbonate (0.2 mole), salicylic aldehyde (0.1 mole) and ethanol (200 cc). The mixture is refluxed for 5 hours, with vigorous stirring. The initially yellow reaction medium turns brown during the heating step. The reaction mixture is then allowed to cool and the resulting precipitate is suction filtered. The alcohol is removed in vacuo. The resulting material is taken up into ethyl acetate, after which it is washed to neutral pH, dried and evaporated. The distilled residue gives a thick oil, b.p.$_{0.05}$ = 210°–220°C. A second distillation gives the pure product (Yield: 25%).

e. Preparation of 2-[3-(2-benzofuroyl)-phenyl]-propionic acid

The above ester (0.05 mole) dissolved in methyl alcohol is saponified with sodium hydroxide (0.15 mole) dissolved in the minimum amount of water, at room temperature, after 24 hours. The alcohol is removed. Water and ether are added. The aqueous phase is made acidic with 2N HCl and is then extracted with ether. The latter ether phase is washed with water and evaporated, to give a residue which is recrystallized from a small amount of methanol (Yield: 80%) as a white powder, m.p. = 140°C.

EXAMPLE 2

[4-(2-benzofuroyl)-phenyl]acetic acid

I. $R_1 = R_2 = R_3 = R_4 = H$ a. Ethyl 4-(α-bromo-acetyl)-phenyl acetate

Ethyl para-acetyl-phenyl acetate is brominated according to the technique described in Example 1(c) to give an oil which is used without further purification.

b. Ethyl 4-(2-benzofuroyl)-phenyl acetate

Ethyl 4-(α-bromo-acetyl)-phenyl acetate (0.05 mole) is mixed with potassium carbonate (0.1 mole), salicylic aldehyde (0.5 mole) and ethanol (120 ml).

Subsequent treatment according to the technique described in Example 1(d) followed by distillation (b.p.$_{0.1}$ = 215°–225°C) gives a thick oil which is crystallized from ethanol, m.p. = 61°–63°C.

c. 4-(2-Benzofuroyl)-phenyl acetic acid is obtained by saponification of the corresponding ester. The acid melts at 160°–161°C.

EXAMPLE 3

[3-(2-Benzofuroyl)-phenyl]acetic acid

I. $R_1 = R_2 = R_3 = R_4 = H$

The compound is prepared as described in Example 2. The acid melts between 130° and 134°C.

EXAMPLE 4

2-[4-(2-Benzofuroyl)-phenyl]propionic acid

I. $R_1 = CH_3; R_2 = R_3 = R_4 = H$

The compound is prepared according to the techniques described in Example 1. It melts at 179°C.

EXAMPLE 5

4-[2-(3-Methyl-benzofuroyl)]-phenyl acetic acid

I. $R_1 = R_2 = R_4 = H; R_3 = CH_3$

Ethyl 4-(α-bromo-acetyl)-phenyl acetate (0.15 mole) is mixed with dry potassium carbonate (0.3 mole), ortho-hydroxy-acetophenone (0.15 mole) and ethanol (300 ml). The resulting mixture is refluxed for 6 hours, with vigorous stirring. Treatment according to the above-described technique is followed by distillation of the residue, b.p.$_{0.1}$ = 220°–225°C (Yield: 20%).

Ethyl 4-[2-(3-methyl-benzofuroyl)]-phenyl acetate is saponified to the corresponding acid. M.p. = 152°C.

EXAMPLE 6

Preparation of 2-[3-(2-benzofuroyl)-4-methoxy-phenyl]propionic acid

I. $R_1 = CH_3; R_2 = OCH_3; R_3 = R_4 = H$ a. Ethyl 2-(3-acetyl-4-methoxy-phenyl)-propionate This compound is prepared by a Friedel-Crafts reaction between ethyl 2-(4-methoxy-phenyl)propionate and acetyl chloride.

The reaction and the treatment are effected according to the usual technique. B.p.$_{0.01}$ = 125°–140°C.

b. The corresponding α-bromo-acetyl derivative is obtained according to the method described in Example 1(c) as a thick oil which is used crude, without further purification.

c. Preparation of ethyl 2-[3-(2-benzofuroyl)-4-methoxy-phenyl]-propionate.

Cyclisation between the bromo-derivative and salicylic aldehyde is effected under the conditions described in Example 1(d) (see the characteristics in following Table 1).

EXAMPLE 7 and EXAMPLE 8

See following Table I.

TABLE I

[Structure: R_4-(benzofuran with R_3)-CO-(phenyl with R_2)-CH(R_1)-COOR]

| Example No. | R | $R_1$ | $R_2$ | $R_3$ | $R_4$ | Yield | Characteristics | |
|---|---|---|---|---|---|---|---|---|
| 6 | Et | $CH_3$ | $OCH_3$ | H | H | 36% | Oil: | $b.p._{0.01}$ = 240–250°C |
|   | H | $CH_3$ | $OCH_3$ | H | H | 80% |  | M.P.=160–162°C |
|   | Et | $CH_3$ | H | H | 5-OMe | 27% | Oil: | $b.p._{0.01}$ = 240–246°C |
| 7 | H | $CH_3$ | H | H | 5-OMe | 80% |  | M.p.=178–180°C |
|   | Et | $CH_3$ | H | H | 6-OMe | 24% | Oil: | $b.p._{0.01}$= 240–245°C |
| 8 | H | $CH_3$ | H | H | 6-OMe | 71% |  | m.p.=about 90°C |

EXAMPLE 9 d-2-[3-(2-Benzofuroyl)-phenyl]propionic acid

Racemic 2-[3-(2-benzofuroyl)-phenyl]propionic acid (0.01 mole) and 1,α-methyl benzylamine (0.01 mole) are dissolved in ethyl acetate. The white crystals which precipitate slowly are suction filtered and are then submitted to three recrystallizations. The salt melts at 145°–146°C.

The resulting acid, the d optical isomer, is obtained by conventional treatment. This acid melts at 125°–126°C. $[\alpha]_D^{22} = +26°$ (methanol).

EXAMPLE 10 l-2-[3-(2-Benzofuroyl)-phenyl]propionic acid

Same treatment as above, but using d,α-methyl-benzylamine. The salt with this amine melts at 145°–146°C. This l-acid melts at 126°C; $[\alpha]_D^{22} = -27°$ (methanol)

The compounds of this invention have a low toxicity and possess a very useful analgesic and anti-inflammatory activity.

Said properties are evidenced by means of the various toxicological and pharmacological tests reported below:

a. Acute toxicity

Acute toxicity is determined by oral administration of the test material in fasting mice and rats.

The compound of Example 1 is homogeneously suspended in a carrier comprising a 3% gum arabic solution.

The animals are kept under observation during 14 days after the treatment.

| $LD_{50}$ in rats | 1,300 mg/kg |
|---|---|
| $LD_{50}$ in mice | 2,500 mg/kg | b. Analgesic activity

Siegmund Test (Proc. Soc. Exp. Biol. Med., 1957, 95, 729-31)

Intraperitoneal injection of 0.25 ml of an aqueous-alcoholic 2-phenyl-1,4-benzoquinone solution at a concentration of 0.02% induces in mice a specific syndrome characterized by the stretching of the hind paws and writhing movements of the trunk.

The tests are carried out with homogeneous lots of 20–30 mice having an average weight of 20 g.

The animals are administered the test material at time zero. One hour later, phenylbenzoquinone is administered by the intraperitoneal route. The animals are individually kept under observation during 5 minutes, between the fifth and the tenth minute after phenylbenzoquinone injection. The number of stretching movements exhibited by each animal during the observation period is recorded.

The present activity of the test material is evaluated by comparing the number of writhing movements of the treated animals with respect to the reference animals.

c. Anti-inflammatory activity

1- Acute carrageenin-induced edema (Winster C. A., Risley E. A., Nuss G.W., Proc. Soc. Biol. Med., 1962, 3, 544–7)

Subplantar injection in the paw of rats of 0.05 ml of an aqueous gel containing 1% carrageenin induces a local edema which may be measured by means of an electric mercury plethysmometer.

Determination of the volume of the forepaw prior, and three hours after the carrageenin injection, makes it possible to calculate the percent inflammation.

The treatment is administered orally, one hour prior to carrageenin administration.

The tests are conducted only with homogeneous lots of 10 male rats weighing 180 g ± 10 g.

The resulting edema is evaluated for each animal by means of the ratio:

$$\frac{V_i - V_o}{V_o}$$

in which:

$V_i$ = volume of the paw at time 3 hrs
$V_o$ = volume of the paw at time zero

The protection noted under the effect of the test material may be evaluated by comparing the percent edema determined in the treated lot with respect to the reference lot.

2 - Turfyl nicotinate (Trafuril) -induced erythema

A slight modification of the HAINING method (Br. Jl. Pharmacol., 1963, 21, 104–12) is used:

The test is carried out with homogeneous lots of 6–12 male albino guinea-pigs weighing 300–400 g, after careful depilation of the skin of their backs on the previous day.

On the day of the test, a disk for antibiotic sensitivity determination impregnated with a 5% alcoholic Turfyl nicotinate solution is applied during one minute on the lumbar area.

The effect produced is recorded after five minutes.

The results are rated according to an "all or nothing" scale, according to whether or not an erythema appears at the locus of application of the disk.

The treatment is administered orally one hour prior to the test, under an uniform volume of 1 ml/kg body weight; the test materials are homogeneously suspended with 3% gum arabic.

The reference animals are administered an equal volume of carrier.

The percent erythema obtained in the treated animals is compared with that obtained in the simultaneously tested reference lot.

The $ED_{50}$ or percent protection of some of the compounds described is indicated in following Table II.

TABLE 2

| Test material: Compound of | Siegmund | Carrageenin-induced edema | Trafuril |
|---|---|---|---|
| Example 1 | 0.72 mg/kg | 9 mg/kg | 3.6 mg/kg |
| Example 2 | 50 mg:28% | 50 mg:15% | / |
| Example 3 | 10 mg:32% 50 mg:50% | 100 mg:10% | 100 mg:17% |
| Example 4 | 5 mg/kg | 170 mg/kg | 115 mg/kg |
| Example 5 | 50 mg:14% | 100 mg:15% | / |
| Example 6 | ≈ 15 mg/kg | >20 mg/kg | / |
| Example 7 | <60 mg/kg | <20 mg/kg | / |
| Example 9 | < 6 mg/kg | 8 mg/kg | 2.3 mg/kg |
| Example 10 | < 6 mg/kg | ≈11.5 mg/kg | 8 mg/kg |

3 - Adjuvant arthritis

According to the works by PEARSON C. M. (J. Chronic. Dis., 1963, 16, 863–74), JONES R. D. and WARD J. R. (Recent progress in hormone research, vol. XIX, 1963, Ac. Press), WARD T. R., JONES R. S. (Arthritis and Rheumatism, 1962, 5, 557–64).

The tests are carried out in male rats weighing 151 g ± 20 g. On day 0, the animals are given intradermally, at the base of the tail, an 0.05 ml injection of a suspension of *Mycobacterium butyricum* in paraffin oil (12 mg killed microbial bodies/ml). The animals are selected on the 14th day and are distributed into homogeneous lots of 15 animals.

The treatment is administered orally, daily, from the 14th to the 28th day.

The chronic arthritis is evaluated according to two criteria:

Arthritis index, by separate scoring of the injuries (erythema, edema, distortions) of each of the four limbs (according to a scoring scale from 0 to 3; maximum score: 12) in each animal on the 14th day, the 18th day, the 21st day, the 24th day and the 28th day (the scoring is effected blind, by two different experimenters).

Sedimentation rate according to KOWARSKI (pipette held at an angle of 45°; recording time: 30 minutes).

The blood sample is taken by the retro-orbicular route. The determination is effected on the 14th, the 21st and the 28th day.

The statistical analysis is effected by the *t* test for the sedimentation rates and by the U test (Mann and Whitney) for the arthritis index.

In this test, the compound of Example 1 is active at 20 mg/kg.

c. Anti-bradykinine activity

The antagonistic action of the compound described in Example 1 was studied with respect to a Bradykinine-induced bronchoconstriction in guinea-pig (20 γ/kg I.V.).

The technique used was the conventional technique described by KONZETT and ROSSLER (Arch. Exp. Path. Pharmakol., 195, 71–74) and later by HARICHAUX (C.R. Soc. Biol., 158, 12, 2437–2441).

The bradykinine-induced bronchospasm is inhibited by this compound, on I.V. administration, at a dosage of 100 γ/kg.

Therefore the invention provides a pharmaceutical composition having an anti-inflammatory and analgesic activity, said composition containing a therapeutically effective quantity of a component selected from the group consisting of the compounds of formula I and their pharmacologically acceptable salts and esters.

The invention provides also a method for the treatment of inflammatory conditions and pains which comprises administering to a patient a pharmaceutical composition containing an effective quantity of a component selected from the groups consisting of the compounds of formula I and their pharmacologically acceptable salts and esters.

For administration, the active ingredient is generally combined with a pharmaceutically acceptable carrier.

The pharmaceutical composition according to this invention is typically administrable by the oral route (formulated as tablets or capsules, for example) or by the rectal route (suppositories), the active ingredient being combined with the suitable carriers or excipients for such pharmaceutical forms.

In such applications, the pharmaceutical composition is advantageously administered by the oral or rectal routes, for example, at a daily dosage regimen within the range from 0.050 g to 1 g active ingredient.

All formulations suitable for such routes of administration may be used.

We claim:

1. A compound selected from the group consisting of a compound of the formula

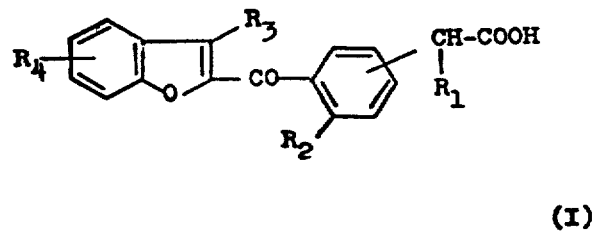

(I)

in which
  $R_1$ is selected from the group consisting of hydrogen and alkyl having 1–6 carbon atoms,
  $R_2$ is selected from the group consisting of hydrogen, alkyl having 1–6 carbon atoms, alkoxy having 1–6 carbon atoms and halogen,
  $R_3$ is selected from the group consisting of hydrogen, alkyl having 1–6 carbon atoms, phenyl and
  $R_4$ is selected from the group consisting of hydrogen, alkyl having 1–6 carbon atoms, alkoxy having 1–6 carbon atoms, hydroxy, halogen and trifluoromethyl and their pharmacologically acceptable salts and lower alkanol esters.

2. A compound as claimed in claim 1, wherein $R_1$ is selected from the group consisting of hydrogen and methyl.

3. A compound as claimed in claim 2, wherein $R_2$ is selected from the group consisting of hydrogen and methoxy, $R_3$ is selected from the group consisting of hydrogen and methyl and $R_4$ is selected from the group consisting of hydrogen and methoxy.

4. 2-[3-(2-benzofuroyl)-phenyl] propionic acid and its pharmacologically acceptable salts and lower alkanol esters.

* * * * *